(12) United States Patent
McDaniel et al.

(10) Patent No.: US 12,012,665 B2
(45) Date of Patent: Jun. 18, 2024

(54) METHOD OF FACILITATING MITIGATION OF COSMETIC IMPERFECTIONS ASSOCIATED WITH FINGERPRINT IMPRESSIONS ON ANODIZED MATERIALS AND ANODIZED MATERIALS TREATED FOR PROVIDING SAME

(71) Applicant: REACTIVE SURFACES, LTD., LLP, Austin, TX (US)

(72) Inventors: Claude Steven McDaniel, Austin, TX (US); Lisa Kay Kemp, Hattiesburg, MS (US); Jonathan Dale Hurt, Austin, TX (US)

(73) Assignee: Reactive Surfaces Ltd., LLP, Austin, TX (US)

( * ) Notice: Subject to any disclaimer, the term of this patent is extended or adjusted under 35 U.S.C. 154(b) by 0 days.

(21) Appl. No.: 18/157,322

(22) Filed: Jan. 20, 2023

(65) Prior Publication Data

US 2023/0160086 A1    May 25, 2023

Related U.S. Application Data

(63) Continuation of application No. 17/211,628, filed on Mar. 24, 2021, now Pat. No. 11,585,006.

(60) Provisional application No. 62/994,985, filed on Mar. 26, 2020.

(51) Int. Cl.
| | |
|---|---|
| *C12N 9/20* | (2006.01) |
| *C09D 7/63* | (2018.01) |
| *C25D 11/24* | (2006.01) |

(52) U.S. Cl.
CPC ............... *C25D 11/24* (2013.01); *C09D 7/63* (2018.01); *C12N 9/20* (2013.01); *C12Y 301/01003* (2013.01)

(58) Field of Classification Search
CPC .................................. C12N 9/20; C25D 11/24
See application file for complete search history.

(56) References Cited

U.S. PATENT DOCUMENTS

| | | | |
|---|---|---|---|
| 6,001,481 | A | 12/1999 | Dearnaley et al. |
| 8,394,618 | B2 | 3/2013 | Buthe et al. |
| 8,932,717 | B2 | 1/2015 | Lee et al. |

*Primary Examiner* — Tekchand Saidha
(74) *Attorney, Agent, or Firm* — David O. Simmons; IVC Patent Agency

(57) ABSTRACT

Disclosed herein are methods specifically tailored for facilitating the mitigation of cosmetic impressions associated with fingerprint impressions on surface(s) of articles of manufacture made from anodized substrates. To this end, such methods provide for removal of fingerprints by enzymatically functionalizing the surface(s) of the article of manufacture (e.g., a cosmetic coating thereof) to generate an enzymatically active surface and activating such enzymatically functionalized surface(s) to promote such fingerprint removal. Thus methods and articles of manufacture made in accordance with such methods provide improved end-use utility and functionality of many products for consumer electronic applications, automotive applications, building materials applications, and the like.

20 Claims, 3 Drawing Sheets

METHOD OF FACILITATING MITIGATION OF COSMETIC IMPERFECTIONS ASSOCIATED WITH FINGERPRINT IMPRESSIONS ON ANODIZED MATERIALS AND ANODIZED MATERIALS TREATED FOR PROVIDING SAME

CROSS-REFERENCE TO RELATED APPLICATIONS

This non-provisional utility patent application claims priority as a continuation from U.S. Provisional Patent Application having Ser. No. 17/211,628, filed 24-Mar. 2021, entitled "METHOD OF FACILITATING MITIGATION OF COSMETIC IMPERFECTIONS ASSOCIATED WITH FINGERPRINT IMPRESSIONS ON ANODIZED MATERIALS AND ANODIZED MATERIALS TREATED FOR PROVIDING SAME," which claims priority from U.S. Provisional Patent Application having Ser. No. 62/917,233, filed 29-Nov. 2018, entitled "METHOD OF FACILITATING MITIGATION OF COSMETIC IMPERFECTIONS ASSOCIATED WITH FINGERPRINT IMPRESSIONS ON ANODIZED MATERIALS AND ANODIZED MATERIALS TREATED FOR PROVIDING SAME", all having a common applicant herewith and being incorporated herein in their entirety by reference.

FIELD OF THE DISCLOSURE

The disclosures made herein relate generally to methods of facilitating mitigation cosmetic imperfections associated with fingerprint impressions and other types of bioorganic stains on materials used in structural and/or cosmetic applications and, more particularly, to methods of facilitating mitigation of cosmetic imperfections resulting from fingerprint impressions on a surface of an anodized materials and to anodized materials treated for providing such cosmetic imperfection mitigation functionality.

BACKGROUND

Anodized materials for structural and cosmetic applications are well known. These applications can include, but are not limited to, consumer electronic applications, automotive applications, building materials used in industrial, commercial and residential applications, and the like. Anodized materials can include certain non-ferrous metals such as, for example, aluminum, magnesium, niobium, titanium and zinc.

Cosmetic appearance is well known to be desirable in consumer electronic applications, automotive applications, building materials used in industrial, commercial and residential applications, and the like (i.e., articles of manufacture). Due to physical handling of such articles of manufacture and associate manual utilization thereof, fingerprint impressions are a common type of contamination on surfaces of such articles of manufacture. This contamination of an article of manufacture is highly undesirable as it is clearly visible to a user and is attributed as a cosmetic defect in the appearance of the article of manufacture. U.S. Pat. No. 8,932,717 entitled LIPOLYTIC ENZYME FOR FORMATION OF ANTI-FINGERPRINT COATING, METHOD OF FORMING ANTI-FINGERPRINT COATING, SUBSTRATE COMPRISING THE ANTI-FINGERPRINT COATING FORMED BY THE METHOD, AND PRODUCT COMPRISING THE SUBSTRATE and U.S. Pat. No. 8,394,618 entitled LIPASE-CONTAINING POLYMERIC COATINGS FOR THE FACILITATED REMOVAL OF FINGERPRINTS, which are both incorporated by reference herein in their entirety, disclose underlying aspects of fingerprints adversely impacting cosmetic appearance of articles of manufacture and proposed approaches for mitigating the visual appearance of such fingerprints on the surface of an affected article of manufacture. However, the disclosures of both of these patents are specific to substrates made of glass and polymeric substrates and are silent on substrates made from a material that can be anodized.

Therefore, methods specifically tailored for facilitating mitigation of cosmetic imperfections resulting from fingerprint impressions on a surface of an anodized material would be desirable and useful.

SUMMARY OF THE DISCLOSURE

Embodiments of the disclosures made herein are directed to methods specifically tailored for facilitating the mitigation of cosmetic impressions associated with fingerprint impressions on surface(s) of articles of manufacture made from anodized substrates. To this end, such methods provide for removal of fingerprints by enzymatically functionalizing the surface(s) of the article of manufacture (e.g., a cosmetic coating thereof) to generate an enzymatically active surface and activating such enzymatically functionalized surface(s) to promote such fingerprint removal. Articles of manufacture treated in accordance with embodiments of the disclosures made herein advantageously exhibit easier and more complete cleaning of fingerprints from surfaces thereof and offer a self-cleaning functionality that result in fingerprint impressions that are not subjected to cleaning becoming less visible over time. In these respects, methods and articles of manufacture configured in accordance with the disclosures made herein provide improved end-use utility and functionality of many products for consumer electronic applications, automotive applications, building materials applications, and the like.

In one or more embodiment of the disclosures made herein, a method of facilitating mitigation of cosmetic imperfections on a surface of an anodized substrate resulting from fingerprint impressions thereon comprises a plurality of steps. A step is performed for providing an anodized substrate comprising a layer of metal oxide. The layer of metal oxide has pores therein. A step is performed for treating a top surface of the layer of metal oxide of the anodized substrate with a composition comprising a lipase to form a lipase-functionalized surface of the anodized substrate. A step is performed for applying a liquid activation composition over at least a portion of the lipase-functionalized surface that is subject to having fingerprint impressions deposited thereon. The liquid activation composition comprises constituent components capable causing a soap composition to be formed on the lipase-functionalized surface in response to at least one of said constituent components being enzymatically degraded by the lipase of the lipase-functionalized surface.

In one or more embodiments, the layer of metal oxide of the anodized substrate has a layer of color-coating composition provided thereon and treating the layer of metal oxide includes applying the lipase-comprising composition over the layer of color-coating composition.

In one or more embodiments, the constituent components of the liquid activation composition capable of causing said soap formation comprises at least one material compositions enzymatically degradable by the lipase of the lipase-functionalized surface to form free fatty acids and metal ions of at least one type of metal.

In one or more embodiments, the at least one material compositions enzymatically degradable by the lipase of the lipase-functionalized surface is a triglyceride.

In one or more embodiments, the metal ions of at least one type of metal comprises metal ions from at least one of sodium and potassium.

In one or more embodiments, the constituent components of the liquid activation composition capable of causing said soap formation comprises at least one material compositions enzymatically degradable by the lipase of the lipase-functionalized surface to form free fatty acids and metal ions of at least one type of metal, the at least one material compositions enzymatically degradable by the lipase of the lipase-functionalized surface is a triglyceride; and the lipase is a triacylglycerol lipase.

In one or more embodiments, the method further comprises determining an approximate pH level at which a target activity level of the lipase of said lipase-comprising composition is obtained and formulating the liquid activation composition to have a pH level about the same as the approximate pH level corresponding to the target activity level of the lipase.

In one or more embodiments, formulating the liquid activation composition comprises mixing an aqueous buffer solution comprising water and a sodium buffer with a triglyceride.

In one or more embodiments, at least a portion of said pores of the layer of metal oxide are exposed at the top surface thereof and treating the top surface of the layer of metal oxide includes causing surfaces defining an interior portion of at least some of said pores of the layer of metal oxide to become at least partially covered with the composition comprising the lipase.

In one or more embodiments, at least a portion of said pores of the layer of metal oxide are exposed at the top surface thereof, treating the top surface of the layer of metal oxide includes causing surfaces defining an interior portion of at least some of said pores of the layer of metal oxide to become at least partially covered with the composition comprising the lipase, at least a portion of said pores of the layer of metal oxide are exposed at the lipase-functionalized surface after treating the top surface of the layer of metal oxide of the anodized substrate with the composition comprising the lipase and applying the liquid activation composition over at least a portion of the lipase-functionalized surface includes causing a layer of the liquid activation composition to be formed over the pores of the layer of metal oxide exposed at the lipase-functionalized surface.

In one or more embodiments, at least a portion of said pores of the layer of metal oxide are exposed at the lipase-functionalized surface after treating the top surface of the layer of metal oxide of the anodized substrate with the composition comprising the lipase and applying the liquid activation composition over at least a portion of the lipase-functionalized surface includes causing a layer of the liquid activation composition to be formed over the pores of the layer of metal oxide exposed at the lipase-functionalized surface.

In one or more embodiments, treating the top surface of the layer of metal oxide of the anodized substrate with a composition comprising a lipase comprises treating the top surface of the layer of metal oxide of the anodized substrate with a triacylglycerol lipase and applying the liquid activation composition over at least a portion of the lipase-functionalized surface comprises applying a buffered oil over at least a portion of the lipase-functionalized surface.

These and other objects, embodiments, advantages and/or distinctions of the present invention will become readily apparent upon further review of the following specification, associated drawings and appended claims.

DETAILED DESCRIPTION

Figure 1:
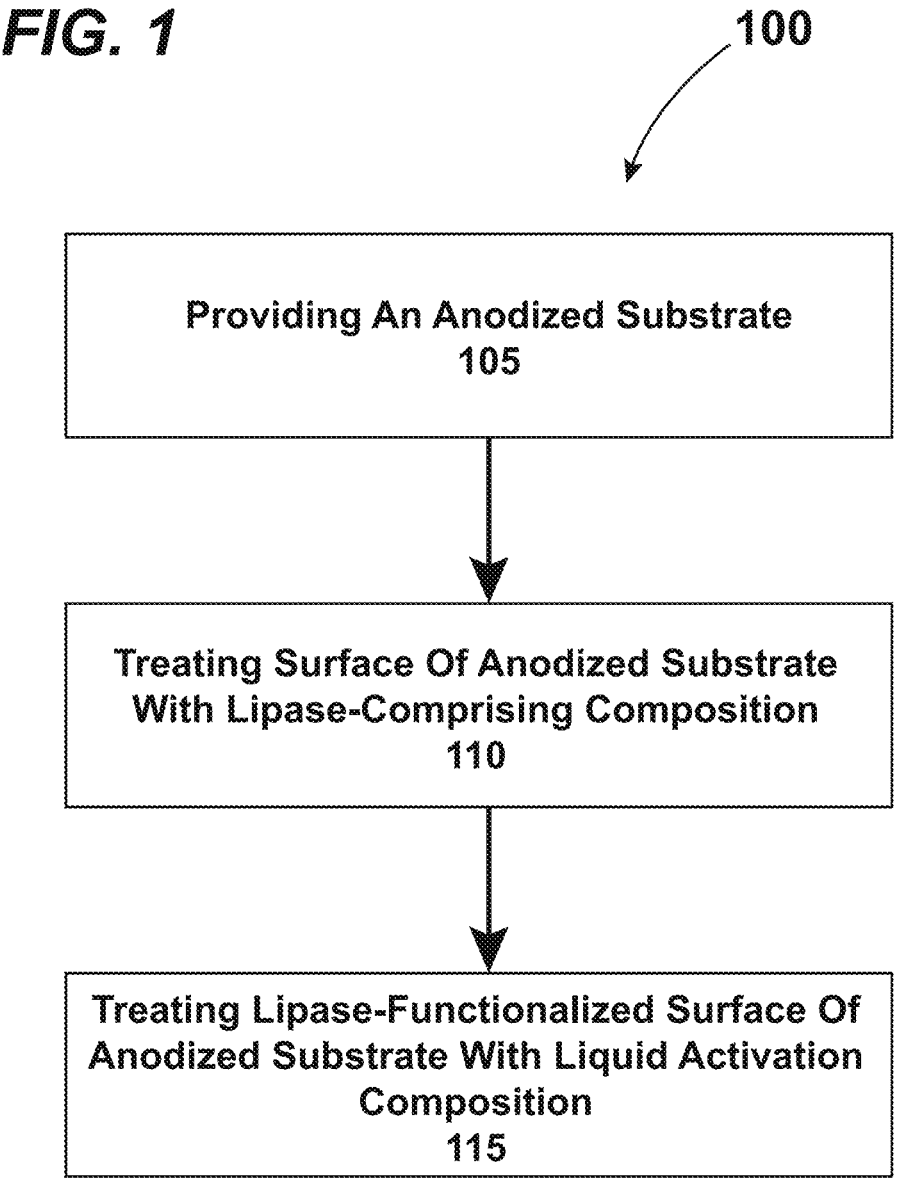
FIG. 1 is a flow diagram showing a method in accordance with an embodiment of the disclosures made herein.

The process of anodizing a substrate of a suitable metal (e.g., aluminum, magnesium, niobium, titanium and zinc) forms a layer of metal oxide that is the result of a chemical reaction between liquid anodizing reagents within which the substrate is anodized. Beneficially, the layer of metal oxide exhibits greater hardness than the underlying un-anodized material of the substrate, thereby enhancing surface durability of the post-anodized substrate. The layer of metal oxide also can enhance coating adhesion properties of the post-anodized substrate due to the layer of metal oxide being porous. U.S. Pat. Nos. 3,964,682; 4,235,582; 4,939,001; 5,478,415; 5,705,225; and 6,001,481, which are all incorporated by reference herein in their entirety, disclose that the layer of metal oxide formed on the surface(s) of an anodized substrate is highly porous and thus susceptible to infiltration by liquids to which the layer of metal oxide is exposed. For example, as discussed and shown in U.S. Pat. No. 5,705,225, anodizing an aluminum substrate with an oxalic acid produces a layer of an aluminum oxide having a generally porous, columnar structure. Similarly, U.S. Pat. No. 6,001,481 discloses that anodizing treatment sometimes results in a porous polygonal cellular microstructure superimposed on a thin (less than 100 nm) "barrier" layer and that the diameter of the pores in the microstructure can be as small as 10 nm with the cell dimension can be as small as about 30 nm.

To produce the layer of metal oxide, the substrate is immersed into an acid electrolyte bath (i.e., the liquid anodizing reagents) within an anodizing tank and an electric current is passed through the substrate. A cathode is mounted to the inside of the anodizing tank and the substrate acts as an anode, whereby oxygen ions are released from the electrolyte to combine with atoms of the substrate at the surface of the substrate being anodized to form the layer of metal oxide. U.S. Pat. No. 3,983,014 entitled ANODIZING MEANS AND TECHNIQUES, which is incorporated by reference herein in its entirety, discloses underlying aspects of anodizing material substrates made from aluminum. U.S. Pat. No. 4,128,461 entitled ALUMINUM HARD ANOD- IZING PROCESS, which is incorporated by reference herein in its entirety, discloses underlying aspects of anodizing material substrates made from aluminum and porosity aspects thereof. U.S. Pat. No. 3,959,091 entitled METHOD OF ANODIZING TITANIUM TO PROMOTE ADHESION, which is incorporated by reference herein in its entirety, discloses underlying aspects of anodizing material substrates made from titanium and porosity aspects thereof.

The layer of metal oxide resulting from the anodizing process is molecularly integrated with the material of the underlying substrate. As a result, the layer of metal oxide is attached to the underlying substrate in a manner that limits its propensity to being washed or worn away. Additionally, in view of the liquid reagent within which the substrate is anodized, it is well known that the layer of metal oxide is generally uniform over the surface areas of the substrate and is a porous structure that allows for secondary processes such as coating, coloring, sealing and the like.

It is also well known that anodized material substrates such as anodized aluminum are sometimes treated with a coating such as paint for providing various protective properties and/or for cosmetic reasons. Such a coating is known to be provided directly over the layer of metal oxide, which is porous as a result of the anodization process. In addition to such porosity of the layer of metal oxide enhancing surface hardness of the substrate, such porosity can also enhance coating (e.g., paint) adhesion properties of the post-anodized substrate. U.S. Pat. No. 4,894,127 entitled METHOD OF ANODIZING ALUMINUM, which is incorporated by reference herein in its entirety, discloses underlying aspects of anodization post-processes of coating anodized substrates with coating compositions such as paint to enhance cosmetic properties.

Methods and articles configured in accordance with the present disclosures utilize the hydrolytic capability of lipase enzymes to enzymatically degrade lipid-containing material compositions to advantageously facilitate mitigation of cosmetic imperfections resulting from fingerprint impressions on a surface of an anodized materials. This mitigation can be characterized as a fingerprint impression becoming less visible over time without any wiping action, as not leave any appreciable residual impression (i.e., "ghosting") when the surface of the anodized substrate is wiped, or both. As the present inventors discovered, a challenge of achieving such mitigation of cosmetic imperfections resulting from fingerprint impressions is that the layer of metal oxide of an anodized substrate is porous as opposed to being smooth and generally impermeable such as for glass and polymeric surfaces. As discussed below in greater detail and as the present inventors also discovered, without sufficient surface treatment, the porous nature of the layer of metal oxide adversely impacts mitigation of fingerprint impression thereon.

To address this challenge, the present inventors set out to investigate enzymatic functionalization of the layer of metal oxide to facilitate effective and efficient mitigation of cosmetic imperfections of fingerprint impressions from the surface of the anodized substrate—i.e., surface as defined by the layer of metal oxide. At the time of the present inventor's investigation, it was known that constituent components of fingerprint impressions can comprise a material composition excreted from the sebum bland (i.e., such material composition generally referred to as sebum) and that sebum generally comprises one or more lipids such as triglycerides, wax monoesters, fatty acids, squalenes, cholesterols, cholesteryl esters, etc. (H. C. Lee et al., Advances in Fingerprint Technology 2001, 75: Table 3.4 and 77: Table 3.5; K. G. Asano et al., J Forensic Sci, July 2002, 3: col. 1, 6-29; P. W. Wertz, Int. J Cosmet. Sci. 2009, 31: 21-25; G. M. Mong et al., Pacific Northwest National Laboratory 1999, 6: 9-26). It is disclosed herein that a fingerprint can also comprise or consist of one or more constituent components carried by a finger or other body part (e.g., palm of a hand) but residing on the finger by virtue of contact of the finger with supply of such one or more constituent components external to a body comprising the finger. For example, such one or more constituent components external to the body can be a food item that is handled by a person's hand. Food items are well known to include lipid-containing materials such as various types of oil and fat from plants and animals.

Accordingly, the present inventors contemplated that enzymatic functionalization of a layer of metal oxide of an anodized substrate with lipase could be used to facilitate mitigation of cosmetic imperfections of fingerprint impressions from the surface of the anodized substrate. More specifically, the present inventors contemplated that enzymatic functionalization of the layer of metal oxide with lipase enzyme could enzymatically break down lipid-based components of fingerprint impressions (i.e., naturally-occurring fingerprint residues) and fingerprint-simulating material compositions utilized in its investigations by catalyzing the hydrolysis of such lipid-based components. This hydrolysis of the lipid-based components is known to create free fatty acids and a glycerol. (Enzyme Nomenclature 1984, Academic Press Inc., 272: 3.1.1.3).

However, during this investigation, it was determined that porosity of the anodized aluminum substrate resulted in less than preferred fingerprint impression mitigation (i.e., residual fingerprint impression remaining) when the anodized aluminum substrate is simply treated in accordance with known techniques of immobilizing a lipase on the surface of the anodized aluminum substrate and such substrate subsequently being subject to a fingerprint. U.S. Pat. No. 8,932,717 entitled LIPOLYTIC ENZYME FOR FORMATION OF ANTI-FINGERPRINT COATING, METHOD OF FORMING ANTI-FINGERPRINT COATING, SUBSTRATE COMPRISING THE ANTI-FINGERPRINT COATING FORMED BY THE METHOD, AND PRODUCT COMPRISING THE SUBSTRATE and U.S. Pat. No. 8,394,618 entitled LIPASE-CONTAINING POLYMERIC COATINGS FOR THE FACILITATED REMOVAL OF FINGERPRINTS, which are all incorporated by reference herein in their entirety, disclose providing an active layer of lipolytic enzyme such as a lipase on the surface of a substrate or coating thereon (e.g., via immobilization) for facilitating mitigation of cosmetic imperfections associated with fingerprint impressions from substrates made from materials that cannot be anodized and that do not have a porous surface structure such as that resulting from anodization.

Based on the present inventor's investigation, they discovered a method of treating a lipase-functionalized (i.e., enzymatically-functionalized) surface of an anodized aluminum substrate to mitigate cosmetic imperfections associated with fingerprint impressions deposited on such surface. Specifically, the present inventors discovered that application of liquid activation composition (e.g., a contiguous or non-contiguous layer) on the lipase-functionalized surface of the anodized aluminum substrate served to improve such mitigation of cosmetic imperfections associated with fingerprint impressions (e.g., residue from naturally-occurring fingerprint residue and simulated fingerprint residue) deposited on the lipase-functionalized surface and to improve color density of a protective and/or cosmetic coating on the as-anodized surface of the aluminum substrate. The liquid activation composition comprised a triglyceride (i.e., olive oil—i.e., a lipid composition) and sodium ions (i.e., a metal ions) simulating corresponding portions of the constituent components of a fingerprint impression—i.e., an example of the above-mentioned fingerprint-simulating material composition. The lipase hydrolyzes the triglyceride to produce free fatty acids, as is well known and discussed above, and the free fatty acids molecularly combines with the sodium ions to produce a water-soluble soap (i.e., a surfactant) exhibiting greater solubility than the triglyceride.

Other formulations for the liquid activation composition are contemplated. A triglyceride used in the liquid activation composition may comprise one or more fatty acids (e.g., a polyunsaturated fatty acid, a monounsaturated fatty acid, a saturated fatty acid, fatty acids having different carbon backbone lengths, etc.). The fatty acid composition may be selected to be optimized for a particular geographic and/or demographic region to match available oil compositions (i.e., triglycerides) of the region. Metal ions can be selected to produce a particular type or configuration of soap. For example, metal ions such a $Ca^{++}$ (Calcium) and $Mg^{++}$ (Magnesium) generally produce a hard soap, while metal ions such as K+ (Potassium) and $Na^+$ (Sodium) typically produce a soft soap. Water-based citrate buffer, different buffers, and different metal ions may be selected to produce different surfactant properties of soap. In one or more embodiments, the liquid activation composition can be in the form of a paste, gel, or material that includes a liquid and that is flowable under pressure.

Without wishing to be constrained to any limiting theory, observations by the present inventors indicated that treatment of the lipase-functionalized surface of the anodized aluminum substrate with the layer of the liquid activation composition served to fill cavities defining porosity of the surface of the anodized aluminum substrate with the soap and to provide a contiguous layer of the soap over the surface of the anodized aluminum substrate and fully or partially filling the pores within the metal oxide layer of the anodized aluminum substrate. Further observations by the present inventors indicated that the resulting layer of soap on the lipase-functionalized surface of the anodized aluminum substrate served to solubilize some or all of the constituent components of fingerprint impressions subsequently deposited onto/into the soap-covered surface of the anodized aluminum substrate. Based on these observations, the present inventors believe that some or all of the constituent components of the subsequently-deposited fingerprint impressions becomes at least partially dissolved by and into the layer of soap and that the layer of soap causes lipid-containing constituent components of the now-dissolved fingerprint components to be enzymatically degraded and to form additional soap—i.e., the free fatty acids formed via hydrolysis of such lipid-containing constituent components becoming molecularly combined with salts within the fingerprint impression and/or liquid activation composition.

Such belief of the present inventors was supported by their observation that the application of the liquid activation composition and associated production of the layer of soap on the surface of the anodized aluminum substrate resulted in the subsequently-deposited fingerprint impressions provided on such soap-covered surface of the anodized aluminum substrate to become less visible over time and to not leave any appreciable residual impression (i.e., "ghosting") when the surface of the anodized aluminum substrate was wiped (i.e., jointly, the resulting performance of the control). The present inventors contemplated the resulting performance of the inventively treated anodized substrate (i.e., having a contiguous layer of soap on the surface) was due to one or more of the following considerations: 1.) the layer of soap was causing the constituent components of the fingerprint impression to become more uniformly distributed over a respective portion of the anodized substrate in view of solubility of the layer of soap, 2.) such uniform distribution of the constituent components of the fingerprint impression subject to enzymatic degradation causing more uniform enzymatic degraded over such respective portion of the anodized substrate by the lipase, and 3.) desirable wiping and removal of enzymatic breakdown components of the fingerprint impression and residual fingerprint components not subject to enzymatic degradation in view of wiping across/into a smooth, effectively non-porous surface as opposed to a porous surface. Accordingly, in the presence of a layer of soap resulting from the liquid activation composition, soap that resulted from hydrolysis of lipid-containing components of a fingerprint impression by the lipase and unhydrolyzed portions of the fingerprint impression would become at least partially distributed within the layer of soap resulting from the liquid activation composition, thereby losing all or part of the ridged-appearance of the fingerprint impression and, thus, becoming less visually apparent.

In contrast, the present inventors assessed a control in the form of an anodized aluminum substrate having a surface defined by a layer of metal oxide, where the surface was lipase-functionalized but not subjected to treatment with the liquid activation composition. Observations by the present inventors indicated that fingerprint impressions deposited onto the lipase-functionalized surface of such control exhibited only limited reduction in visibility of the fingerprint impressions over time and exhibited an appreciable residual fingerprint impression remaining on the surface of the anodized aluminum substrate when the surface was wiped (i.e., jointly, the resulting performance of the control). Still not wishing to be constrained to any limiting theory, the present inventors contemplated the resulting performance of the control in the absence a layer of soap resulting from the liquid activation composition was due to one or more of the following considerations: 1.) largely non-uniform distribution of constituent components of the fingerprint impression as a result of absence of the layer of soap causing such constituent components of the fingerprint impression to be undissolved, 2.) largely non-uniform enzymatic degradation of the lipid-containing constituent components of the fingerprint impression as a result of absence of the layer of soap causing the fingerprint impression to be undissolved and non-uniformly distributed; and 3.) less than desirable wiping and removal of enzymatic breakdown components of the fingerprint impression and residual fingerprint components in view of wiping across/into a porous surface as opposed to a smooth, effectively non-porous surface. Accordingly, in the absence of a layer of soap resulting from the liquid activation composition, soap that resulted from hydrolysis of lipid-containing components of a fingerprint impression by the lipase and unhydrolyzed portions of the fingerprint impression would tend to not become distributed over the surface of the substrate, thereby maintaining all or part of the ridged-appearance of the fingerprint impression and, thus, remaining more visually apparent.

It is disclosed herein that the degree to which a fingerprint impression and remnants/derivatives thereof are visually apparent on the surface of an anodized substrate (i.e., the layer of metal oxide thereof) can be influenced by one or more characteristics of the fingerprint impression, by one or more characteristics of the surface of the anodized substrate, by one or more visibility-influencing characteristics of material compositions residing on the surface of the anodized substrate (e.g., soap or non-hydrolyzed component of a fingerprint impression), or a combination thereof. Examples of such visibility-influencing characteristics can include, but are not limited to, light refractivity, reflectivity, opacity, physical density, and the like. Accordingly, the degree to which a fingerprint impression and remnants/derivatives thereof are visually apparent on the surface of an anodized substrate can be influenced by a difference between one or more visibility-influencing characteristics of at least two of the following: the layer of metal oxide (or color coating thereon), one or more material compositions formed by enzymatic degradation of one or more constituent components of the fingerprint impression, one or more constituent components of the fingerprint impression that are not subject to enzymatic degradation and one or more material compositions formed by enzymatic degradation of the liquid activation composition. It is also disclosed herein that the degree to which a fingerprint impression and remnants/derivatives thereof are visually apparent on the surface of an anodized substrate (i.e., the layer of metal oxide thereof) can be influenced by a difference between location of different material compositions—e.g., on the surface of the anodized substrate, within a layer of material on the surface of the anodized substrate, and within a pore of a layer of material defining the surface of the anodized substrate.

Presented now is a description of a method in accordance with the present disclosures (methodology 100, as shown in FIG. 1) that is configured for enabling enzymatic functionalization of a surface defined by a layer of metal oxide of an anodized substrate to facilitate effective and efficient mitigation of cosmetic imperfections of fingerprint impressions from the surface of anodized substrate. Advantageously, substrates treated in accordance with the method 100 exhibit the advantageous properties of fingerprint impressions deposited on the surface defined by the layer of metal oxide of the anodized substrate to become markedly less visible over time and such fingerprint impressions not leaving any appreciable residual impression when such surface of the anodized substrate is wiped. These advantageous properties are the result of the method 100 utilizing hydrolysis of lipid-containing components of a liquid activation composition and subsequently deposited fingerprint impressions to provide a layer of soap (i.e., hydrolysis-generated free fatty acid molecularly bonded to available metal ions) on the enzymatically-functionalized surface of the anodized substrate.

Figure 2A:
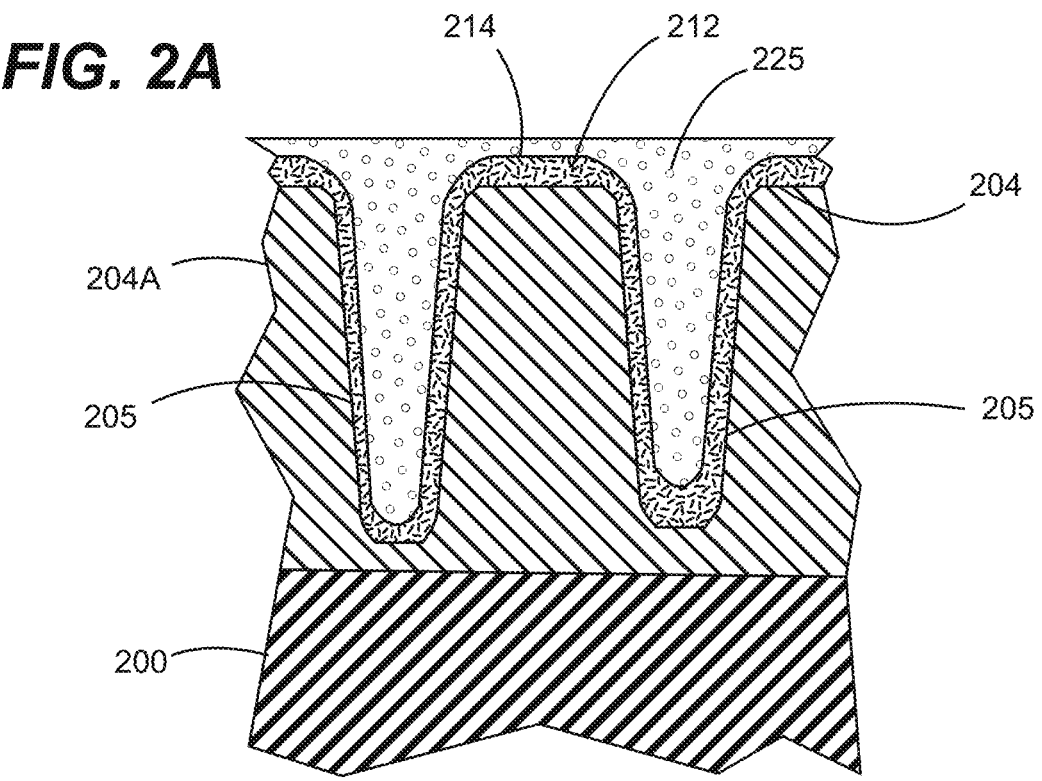
FIG. 2A is a is a cross-sectional diagrammatic view showing an anodized substrate with an enzyme-functionalized surface and applied liquid activation composition in accordance with the disclosures made herein.

Referring to FIG. 1, the method 100 includes a step 105 of providing an anodized substrate 200 shown in FIG. 2A. The anodized substrate 200 has having a surface 204 defined by a layer of metal oxide 204A resulting from anodizing. As a result of anodization, the layer of metal oxide 204A can have pore structures 205 therein (i.e., pores) and the surface 204 of the anodized substrate 200 can include openings to at least a portion of such pore structures 205 therein. Generally, surfaces of a substrate that is anodized to produce the anodized substrate 200 can otherwise be substantially, markedly or generally smooth and non-textured before being anodized. The pore structures 205 contribute to the surface 204 of the anodized substrate 200 having spaces therein (i.e., cavities) that can retain liquid material compositions. The pore structures 205 result in the surface 204 of the anodized substrate 200 exhibit markedly increased porosity as compared to the substrate prior to anodization. Such increased porosity can be characterized as being more porous than that of a material substrate having a smooth and non-textured surface prior to being anodized or as being markedly more porous than that of a material substrate having a markedly less porous surface prior to being anodized. Techniques of anodizing material substrates are discussed above.

Following the step 105, the method 100 provides a step 110 of treating the surface 204 of the anodized substrate 200 with a composition comprising a lipase 212 to thereby provide the lipase on the surface 204 and define a lipase-functionalized surface 214 of the anodized substrate 200 as shown in FIG. 2A. Such the lipase on the surface 204 of the anodized substrate 200 can include the lipase being provided on all or a portion of surfaces defining the pore structures 205 of the layer of metal oxide 204A. It is well known in the art that enzymes, including lipase, can be immobilized on the surface of a material substrate by any number of techniques, including, but not limited to, via covalent bonding to a surface, encapsulation within membrane or permeable substrate, physical adsorption onto a surface, entrapment within a surface coating, and the like. Such immobilization of an enzyme is generally characterized as the enzyme being physically confined or localized in a certain defined region of space with retention of all or a sufficient portion of its catalytic activities. In one or more embodiments, one or more enzymes can be provided on a surface of an anodized substrate (i.e., surface of the layer of metal oxide or a coating provided thereon) by first applying a layer of material imparting a color on the surface of the anodized substrate and then providing the one or more enzymes on such color-imparting material. In one or more other embodiments, the enzyme can be provided on the surface of the anodized substrate by incorporating the one or more enzymes into the color-imparting material prior to applying the layer of color-imparting material on the surface of the anodized substrate.

Lipase, which is a lipolytic enzymes, is useful in methods and articles of manufacture in accordance with the disclosures made herein as lipase catalyzes the hydrolysis (i.e., breaks) ester bonds of lipid substrates. In the context of such methods and articles of manufacture, such lipid substrates can comprise lipid-based components of sebum, lipid-based components of materials external to the body (e.g., food items handled by a person's hand), or a combination thereof. Lipase useful in methods and articles of manufacture in accordance with the disclosures made herein can include, but are not limited to, a lipase derived from *Acinetobacter, Aedes aegypti, Anguillajaponica, Antrodia cinnamomea, Arabidopsis rosette, Arabidopsis thaliana, Arxula adeninivorans, Aspergillus niger, Aspergillus oryzae, Aspergillus tamarii, Aureobasidium pullulans, Avena sativa, Bacillus licheniformis, Bacillus sphaericus, Bacillus stearothermophilus, Bacillus subtilis, Bacillus thermocatenulatus, Bacillus thermoleovorans, Bombyx mandarina, Bombyx mori, Bos Taurus, Brassica napus, Brassica rapa, Burkholderia cepacia, Caenorhabditis elegans, Candida albicans, Candida antarctica, Candida deformans, Candida parapsilosis, Candida rugosa, Candida thermophila, Canis domesticus, Chenopodium rubrum, Clostridium beijerinckii, Clostridium botulinum, Clostridium novyi, Danio rerio, Galactomyces geotrichum, Gallus, Geobacillus, Gibberella zeae, Gossypium hirsutum, Homo sapiens, Kurtzmanomyces sp., Leishmania infantum, Lycopersicon esculentum L, Malasseziafurfur, Methanosarcina acetivorans, Mus musculus, Mus spretus, Mycobacterium tuberculosis, Mycoplasma hyopneumoniae, Myxococcus xanthus, Neosartorya fischeri, Oryctolagus cuniculus, Oryza sativa, Penicillium cyclopium, Phlebotomus papatasi, Pseudomonas aeruginosa, Pseudomonasfluorescens, Pseudomonasfragi, Pseudomonas* sp, *Rattus norvegicus, Rhizomucor miehei, Rhizopus oryzae, Rhizopus stolonifer, Ricinus communis, Samia cynthia ricini, Schizosaccharomyces pombe, Serratia marcescens, Spermophilus tridecemlineatus, Staphylococcus simulans, Staphylococcus xylosus, Sulfolobus solfataricus, Sus scrofa, Thermomyces lanuginosus, Trichomonas vaginalis, Vibrio harveyi, Xenopus laevis, Yarrowia lipolytica*, or a combination thereof.

It is disclosed herein that enzyme useful in methods and articles of manufacture in accordance with the disclosures made herein can include one or more enzymes other than lipase. The benefit of including one or more enzymes other than lipase is that fingerprint impressions often include one or more constituent components that are not enzymatically degraded by a lipase. Examples of such one or more enzymes include, but are not limited to, a protease which breaks down proteins and amylase which breaks down starches. Additionally, other lipolytic enzymes besides lipase can be utilized.

Figure 2B:
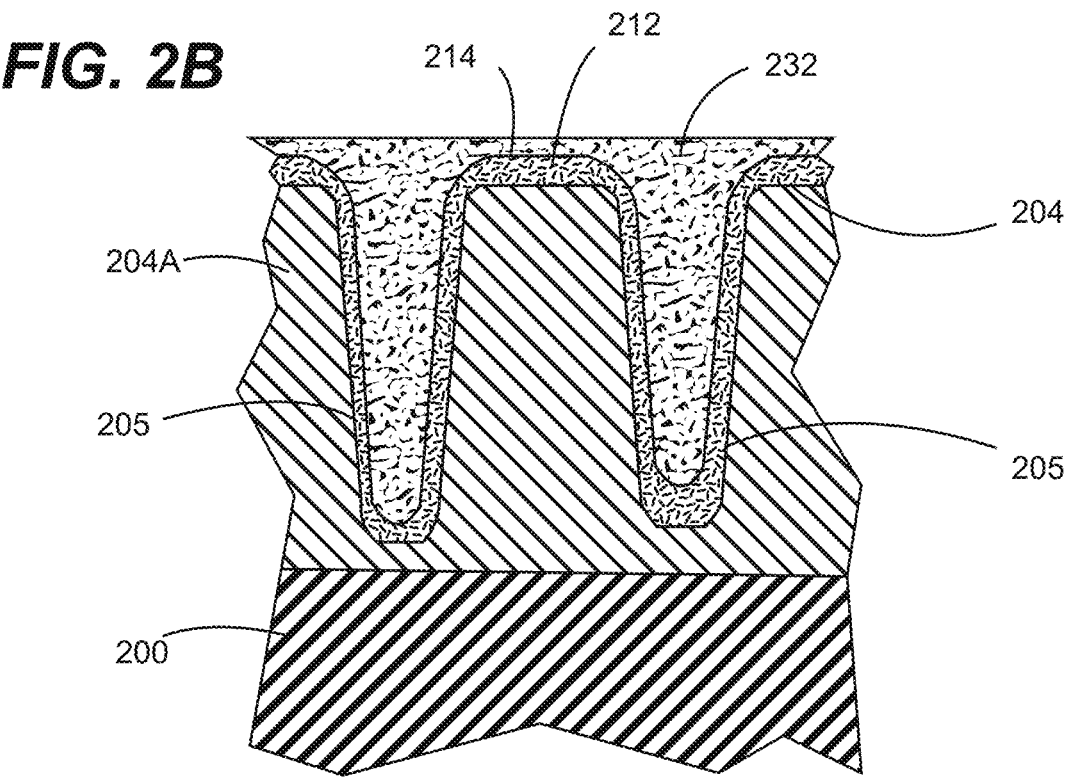
FIG. 2B is a cross-sectional diagrammatic view showing the anodized substrate of FIG. 2A the applied liquid activation composition converted to a soap composition as a result of enzymatic degradation of the applied liquid activation composition by the enzyme of the enzyme-functionalized surface.
Figure 3A:
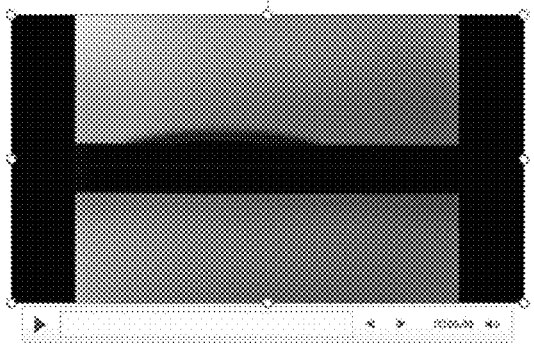
FIGS. 3A-3D are screen-captured images of a video showing time-elapsed result of a droplet of a sodium buffered oil composition deposited onto a metal-oxide surface of an anodized aluminum substrate.
Figure 3B:
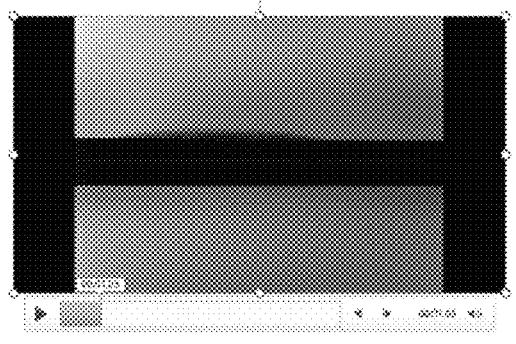
Figure 3C:
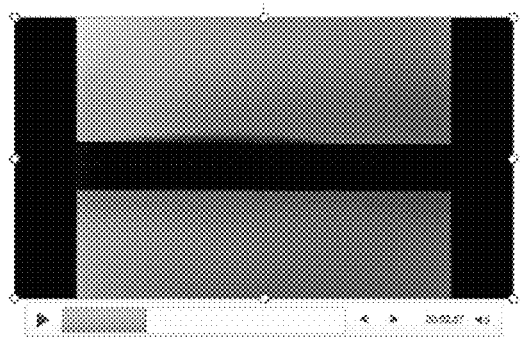
Figure 3D:
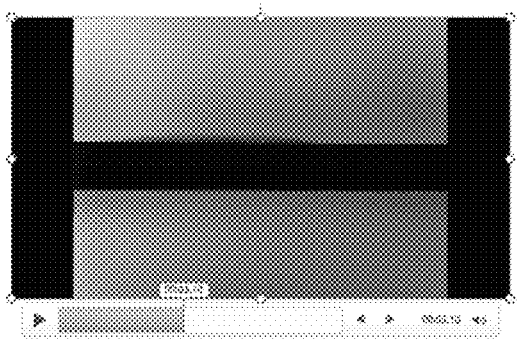

Following the step 110, the method 100 provides a step 115 of treating the lipase-functionalized surface 214 of the anodized substrate 200 with a liquid activation composition 225 as shown in FIG. 2A. Preferably, the liquid activation composition 225 partially fills the pore structures 205 within the layer of metal oxide 204A of the anodized substrate 200 and forms a contiguous layer over the top of the lipase-functionalized surface 214. In one or more embodiments, the surface 204 can be defined by a color-imparting coating or other coating that has previously been applied to the layer of metal oxide 204A of the anodized substrate 200. As discussed above and shown in FIG. 2B, the liquid activation composition 225 (i.e., liquid activation composition in accordance with methods and articles of manufacture in accordance with the disclosure made herein) is acted on by the lipase 212 to provide a layer (preferably contiguous layer) of soap 232 over the surface 204 of the anodized substrate 200 and to fully or partially filling the pore structures 205 within the layer of metal oxide 204A of the anodized substrate 200.

In one or more preferred embodiments, the liquid activation composition 225 comprises one or more lipid-containing compositions and one or more types of metal ions. In some embodiments, the liquid activation composition 225 can include a positive allosteric activator specific to the lipase 212 (or specific to any enzyme provided on the surface 204 of the anodized substrate 200). In use, the lipase 212 hydrolyzes the one or more lipid-containing compositions to produce free fatty acids and at least a portion of the free fatty acids molecularly combine with at least a portion of the one or more sodium ions to produce the soap 232 (i.e., a water-soluble surfactant). Functionally, the soap 232 serves to solubilize some or all of the constituent components of fingerprint impressions subsequently deposited onto/into the soap-covered surface of the anodized substrate 200.

Various aspects of the method and articles of manufacture in accordance with the disclosures made herein are illustrated by the following non-limiting examples. The examples are for illustrative purposes and are not a limitation on any practice of the present invention. It will be understood that variations and modifications can be made without departing from the spirit and scope of the appended claims.

Example 1—Preparation of Buffered Fingerprint Residue Simulation Composition

Commercially-available reagent grade olive oil ["Oil"; source product no. 01514 of Sigma Aldrich®, including Millipore Sigma, Aldrich, Fluka, Supelco and Sigma-Aldrich Fine Chemicals, P.O. Box 14508, Saint Louis, MO 63178 U.S.A.] and various aqueous buffer solutions were used to produce a respective buffered solution of oil ("Buffered Oil"). Buffered Oil of a respective type was prepared by shaking overnight an aqueous buffer solution comprising water and a respective buffer with the Oil to saturate the Oil with the aqueous buffer solution. "Tris Buffered Oil" was produced through use of (trishydroxymethyl) aminomethane ("Tris") buffer providing a pH level of nominally 7.2. "Sodium Buffered Oil" was produced through use of sodium citrate buffer providing a pH level of nominally 8.4.

Example 2—Porosity Assessment of Anodized Panels

Anodized aluminum coupons ("Anodized Panel") with a black-colored coating on its anodized surface were cleaned with Aculon® 905 cleaner ["905 Cleaner"; source Aculon Inc., 11839 Sorrento Valley Road, Suite 901, San Diego, CA 92121, ("Aculon")], thereby providing each of the Anodized Panels with a cleaned anodized surface. According to Aculon, the 905 Cleaner is a water-based cleaner intended for use on aluminum substrates and provides aluminum substrates with a water break free condition to enhance the adhesion of applied coatings. Cleaning of the Anodized Panels was performed in accordance Aculon instructions for the 905 Cleaner. Components of the 905 Cleaner are listed at Table 1.

TABLE 1

| 905 Cleaner Components. | |
| --- | --- |
| Chemical (CAS No.) | Amount |
| Borax (1330-43-4) | 1-5% |
| Sodium polynaphthalenesulfonate (9084-06-4) | 1-5% |
| Pentasodium triphosphate (7758-29-4) | 3-8% |
| Water (7732-18-5) | 85-95% |

Droplets of the Tris Buffered Oil discussed above in Example 1 were placed on the cleaned anodized surface of the Anodized Panel. Starting at the moment that a droplet of the Tris Buffered Oil were placed on the cleaned anodized surface of the Anodized Panel, video recording of the droplet was initiated. Upon review of video recordings of the Tris Buffered Oil droplet placed upon the cleaned anodized surface of the Anodized Panel, it was observed that the cleaned anodized surface of the Anodized Panel absorbed the droplet of the Tris Buffered Oil (as shown in FIGS. 3A-3D at times 0, 1, 2 and 3 minutes, respectively). In view of it being well known that the layer of metal oxide defining the surface of an anodized substrate is porous, as discussed above in reference to references incorporated herein by reference, the present inventors concluded that pores in the anodized surface of the Anodized Panel allowed the droplet of Tris Buffered Oil to infiltrate (e.g., be absorbed, wicked, pulled into, or otherwise accumulate in) at least a portion of underlying and adjacent pores of the Anodized Panel.

This porosity assessment also included a wiping assessment where Tris Buffered Oil droplets were wiped from the anodized surface of the Anodized Panel. It was observed that wiping the applied droplets at a time near to the when the Tris Buffered Oil droplets were applied resulted in markedly more complete removal of such droplets and markedly less residual ghosting (i.e., residual oil staining) than for when applied Tris Buffered Oil droplets were allowed to sit for a period of time (e.g., one minute or longer). In view of the known porosity of the layer of metal oxide defining the surface of an anodized substrate, the present inventors concluded that at least a portion of the applied droplets were that had become entrapped within the pores of the of the Anodized Panel protected such infiltrated portion of the applied droplets from being assessible for cleaning by wiping of the surface of the Anodized Panel.

Example 3—Assessment of Activated Lipase-Functionalized Anodized Panels

Anodized Panels, as described and cleaned in Example 2 above, had their as-cleaned anodized surface coated with an Aculon® RD-A primer ("RD-A Primer"; source Aculon) to produce Anodized Panels that were primed ("Primed Panels"), where such priming was performed in accordance with Aculon instructions for the RD-A Primer. Components of the RD-A Primer are listed at Table 2.

TABLE 2

RD-A Primer Components.

| Chemical (CAS No.) | Amount |
| --- | --- |
| 2-Propanol (67-63-0) | 99-100% |

1 mL of Aculon® XT1 hydrophobic coating ("XT 1 Coating") was mixed with 100 µl of Biocat Lipase L ["Lipase"; source BIO-CAT, Inc., 9117 Three Notch Road, Troy, Virginia 22974 U.S.A. ("BioCat")] to produce a lipase-functionalizing coating ("Lipase Coating").

After curing of the RD-A Primer applied in Example 1, the Lipase Coating was applied to the surface of the Primed Panels to produce test panels that were lipase-functionalized ("Lipase-Functionalized Panels"), where such application was performed in accordance with Aculon instructions for the XT 1 Coating. Components of the XT 1 Coating and characteristics of the lipases are shown in Tables 3 and 4, respectively.

TABLE 3

XT1 Coating Components

| Chemical (CAS No.) | Amount |
| --- | --- |
| 2-Propanol (67-63-0) | >98% |

TABLE 4

Lipase

| Chemical (CAS No.) | Characteristics |
| --- | --- |
| LipaseL (9001-62-1) | <5% by weight lipase, enzymatically active pH 7-11, and active between about 20° C.-60° C. |

Sodium Buffered Oil discussed above in Example 1 was applied the surface of Lipase-Functionalized Panels prepared as described above to produce test panels having a liquid activation composition coating thereon ("Activated Lipase-Functionalized Panels"). As discussed above in reference to Example 1, the Sodium Buffered Oil exhibited a pH level of nominally 8.4, which is notable in view of it being determined that the Lipase used in Lipase Coating had an activity maximum at about a pH level of about 8.4. Lipase-Functionalized Panels without the Sodium Buffered Oil applied thereto were used as controls ("Lipase-Functionalized Control Panels"). Visually, the Activated Lipase-Functionalized Panels exhibited a darker, more deep coloration than the Lipase-Functionalized Control Panels.

Various types and configurations of stains ("Stains") were applied to the surface of the Activated Lipase-Functionalized Panels and the Lipase-Functionalized Control Panels. These Stains included: a fingerprint impression from a finger, a fingerprint impression from a finger after wiping the finger on a person's forehead, a fingerprint impression from a finger after dipping the finger in Oil discussed above in Example 1, a fingerprint impression from a finger after dipping the finger in Sodium Buffered Oil discussed above in Example 1, a fingerprint impression from a finger after dipping the finger in Tris Buffered Oil discussed above in Example 1, and a droplet of Sodium Buffered Oil.

The Stains applied to the Activated Lipase-Functionalized Panels were less visible than the Stains applied to the Lipase-Functionalized Control Panels. The Stains applied to the Activated Lipase-Functionalized Panels were easier to remove by wiping with a Kimwipe Lab Towel (Kimwipe®, source Kimberly-Clark Corporation, 351 Phelps Drive; Irving, Texas 75038, U.S.A.). It was observed that some or all of ghost fingerprint image were inhibited for the Activated Lipase-Functionalized Panels, whereas a significant degree of ghost fingerprint image was exhibited for the Lipase-Functionalized Control Panels.

Although the invention has been described with reference to several exemplary embodiments, it is understood that the words that have been used are words of description and illustration, rather than words of limitation. Changes may be made within the purview of the appended claims, as presently stated and as amended, without departing from the scope and spirit of the invention in all its aspects. Although the invention has been described with reference to particular means, materials and embodiments, the invention is not intended to be limited to the particulars disclosed; rather, the invention extends to all functionally equivalent technologies, structures, methods and uses such as are within the scope of the appended claims.

What is claimed is:

1. A product exhibiting mitigation of cosmetic imperfections on a surface of an anodized substrate thereof, the product made by a process comprising:
    treating a surface of an anodized substrate with a composition comprising lipase to form a lipase-functionalized surface of the anodized substrate, wherein the surface of the anodized substrate comprises metal oxide having cavities therein; and
    applying an activation composition over at least a portion of the lipase-functionalized surface that is subject to having a lipid-containing contaminant deposited thereon, wherein the activation composition comprises constituent components capable causing a soap composition to be formed on the lipase-functionalized surface in response to at least one of said constituent components being enzymatically degraded by said lipase of the lipase-functionalized surface.

2. The product of claim 1 wherein:
    the metal oxide has a color-coating composition integral therewith; and
    said treating the surface of anodized substrate includes applying the lipase-comprising composition over the color-coating composition.

3. The product of claim 1 wherein said constituent components of the activation composition capable of causing said soap formation comprises:
at least one material compositions enzymatically degradable by said lipase of the lipase-functionalized surface to form free fatty acids; and
metal ions of at least one type of metal.

4. The product of claim 3 wherein the at least one material compositions enzymatically degradable by said lipase of the lipase-functionalized surface is triglyceride.

5. The product of claim 3 wherein said metal ions of at least one type of metal comprises metal ions from at least one of sodium and potassium.

6. The product of claim 1 wherein:
said constituent components of the activation composition capable of causing said soap formation comprises at least one material compositions enzymatically degradable by said lipase of the lipase-functionalized surface to form free fatty acids and metal ions of at least one type of metal;
the at least one material compositions enzymatically degradable by said lipase of the lipase-functionalized surface is triglyceride.

7. The product of claim 1, wherein the process further comprises:
determining an approximate pH level at which a target activity level of said lipase of said lipase-comprising composition is obtained; and
formulating the activation composition to have a pH level about the same as the approximate pH level corresponding to the target activity level of said lipase.

8. The product of claim 7 wherein formulating the activation composition comprises mixing an aqueous buffer solution comprising water and a sodium buffer with triglyceride.

9. The product of claim 1 wherein:
at least a portion of said cavities are exposed at the surface of the anodized substrate; and
treating the surface of the anodized substrate includes causing surfaces defining an interior portion of at least some of said cavities to become at least partially covered with the composition comprising said lipase.

10. The product of claim 9 wherein said constituent components of the activation composition capable of causing said soap formation comprises:
at least one material compositions enzymatically degradable by said lipase of the lipase-functionalized surface to form free fatty acids; and
metal ions of at least one type of metal.

11. The product of claim 1 wherein:
at least a portion of said cavities are exposed at the surface of the anodized substrate;
treating the surface of the anodized substrate includes causing surfaces defining an interior portion of at least some of said cavities to become at least partially covered with the composition comprising said lipase;
at least a portion of said cavities are exposed at the lipase-functionalized surface after treating the surface of the anodized substrate with the composition comprising said lipase; and
applying the activation composition over at least a portion of the lipase-functionalized surface includes causing a layer of the activation composition to be formed over ones of said cavities exposed at the lipase-functionalized surface.

12. The product of claim 11 wherein said constituent components of the activation composition capable of causing said soap formation comprises:
at least one material compositions enzymatically degradable by said lipase of the lipase-functionalized surface to form free fatty acids; and
metal ions of at least one type of metal.

13. The product of claim 12 wherein the process further comprises:
determining an approximate pH level at which a target activity level of said lipase of said lipase-comprising composition is obtained; and
formulating the activation composition to have a pH level about the same as the approximate pH level corresponding to the target activity level of said lipase.

14. The product of claim 13 wherein formulating the activation composition comprises mixing an aqueous buffer solution comprising water and a sodium buffer with triglyceride.

15. The product of claim 1 wherein:
at least a portion of said cavities are exposed at the lipase-functionalized surface after treating the surface of the anodized substrate with the composition comprising said lipase; and
applying the activation composition over at least a portion of the lipase-functionalized surface includes causing a layer of the activation composition to be formed over ones of said cavities exposed at the lipase-functionalized surface.

16. The product of claim 15 wherein said constituent components of the activation composition capable of causing said soap formation comprises:
at least one material compositions enzymatically degradable by said lipase of the lipase-functionalized surface to form free fatty acids; and
metal ions of at least one type of metal.

17. The product of claim 1 wherein:
treating the surface of the anodized substrate with a composition comprising a lipase comprises treating the surface of the anodized substrate with at least triacylglycerol lipase; and
applying the activation composition over at least a portion of the lipase-functionalized surface comprises applying a buffered oil over at least a portion of the lipase-functionalized surface.

18. The product of claim 17 wherein the process further comprises:
determining an approximate pH level at which a target activity level of said lipase of said lipase-comprising composition is obtained; and
formulating the buffered oil to have a pH level about the same as the approximate pH level corresponding to the target activity level of said lipase.

19. The product of claim 18 wherein formulating the buffered oil comprises mixing an aqueous buffer solution comprising water and a sodium buffer with triglyceride.

20. The product of claim 18 wherein the buffered oil comprises:
at least one material compositions enzymatically degradable by said lipase of the lipase-functionalized surface to form free fatty acids; and
metal ions of at least one type of metal.

* * * * *